Figure 1:
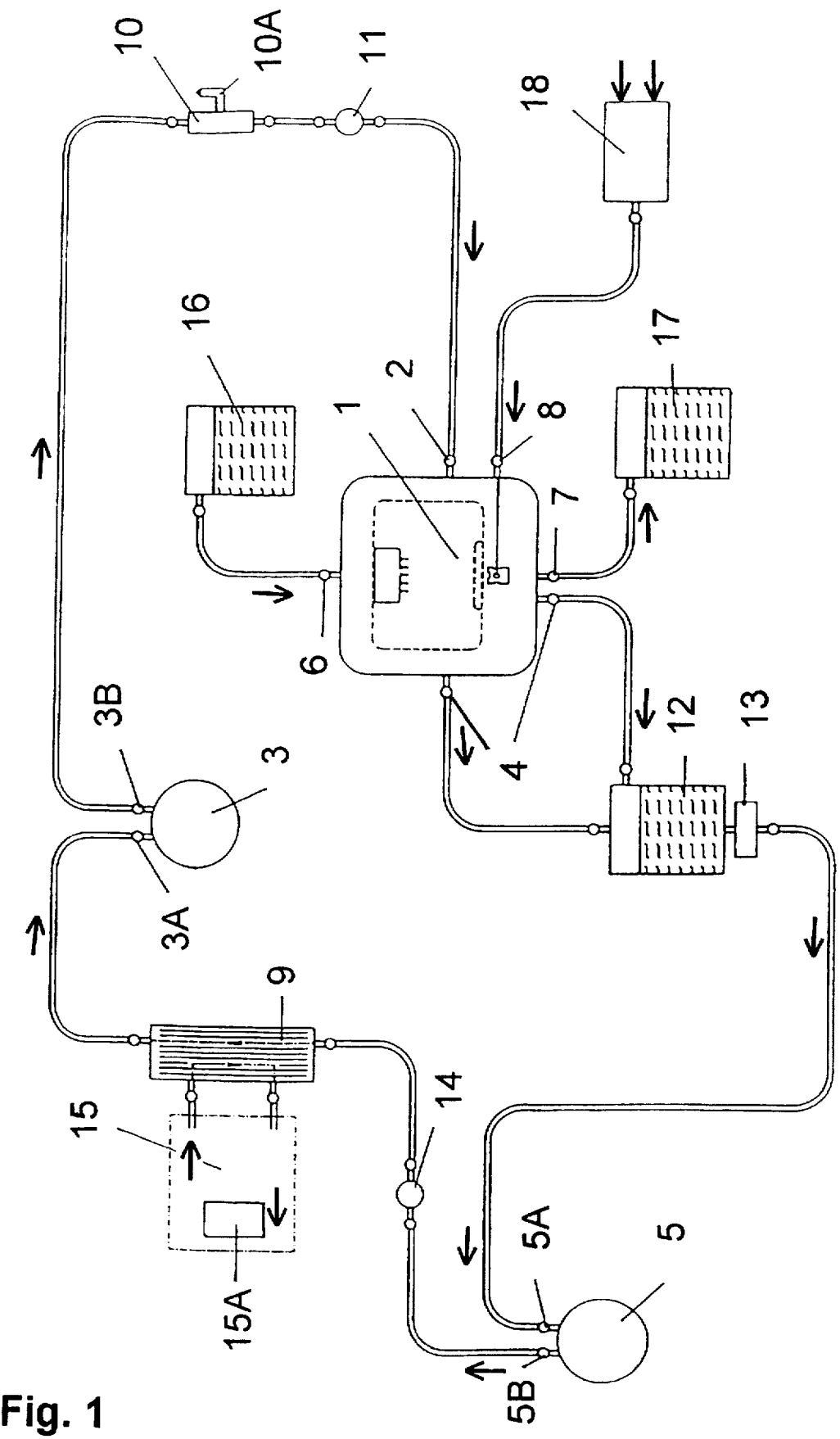

United States Patent [19]

Mayer

[11] Patent Number: 5,786,136

[45] Date of Patent: Jul. 28, 1998

[54] METHOD AND DEVICE FOR CONSERVING ORGANS, BODY EXTREMITIES AND PIECES OF BODY TISSUE

[76] Inventor: Berndt Mayer, Otto-Suhr-Allee 106 c, D-10685 Berlin, Germany

[21] Appl. No.: 553,278

[22] PCT Filed: Jun. 6, 1994

[86] PCT No.: PCT/EP94/01839

§ 371 Date: Nov. 28, 1995

§ 102(e) Date: Nov. 28, 1995

[87] PCT Pub. No.: WO94/28710

PCT Pub. Date: Dec. 22, 1994

[30] Foreign Application Priority Data

| Jun. 7, 1993 | [DE] | Germany | 43 19 368.4 |
| Nov. 9, 1993 | [DE] | Germany | 43 39 024.2 |
| Mar. 4, 1994 | [DE] | Germany | 44 07 863.3 |

[51] Int. Cl.$^6$ ................................... A01N 1/02
[52] U.S. Cl. ..................... 435/12; 435/284.1; 435/818
[58] Field of Search ................. 435/1.1, 1.2, 284.1, 435/818

[56] References Cited

U.S. PATENT DOCUMENTS

| 3,738,914 | 6/1973 | Thorne et al. | 435/284.1 |
| 3,772,153 | 11/1973 | De Roissart | 435/284.1 |
| 5,472,876 | 12/1995 | Fahy | 435/284.1 |

Primary Examiner—David A. Redding
Attorney, Agent, or Firm—Londa and Traub LLP

[57] ABSTRACT

Described is a method and device for conserving organs, body extremities and pieces of body tissue by means of an extracorporal circulation system. Conservation is carried out at room temperature or body temperature. Long-term conservation is carried out using three discrete circulation systems, the first supplying the organs, extremities or pieces of tissue with an aqueous physiological nutrient concentrate or with blood or with a blood product. The oxygen is physically dissolved and supplied through a dialysis membrane by the second circulation system, metabolite exchange and detoxication also taking place at this membrane. The third circulation system cuts in automatically, under timer control, to flush out the tissue. During flushing, circulation system (1) and (2) are switched off in order to avoid the liquids mixing with each other. The various elements of the device are connected up by means of disposable tubing or tubing made of sterilizable material. The tissue is protected from microbial contamination by an organ enclosure.

20 Claims, 3 Drawing Sheets

METHOD AND DEVICE FOR CONSERVING ORGANS, BODY EXTREMITIES AND PIECES OF BODY TISSUE

The present invention relates to a method of and a device for conserving organs, body extremities resp lobes of body tissue and can specifically be applied for keeping organs, body extremities and lobes of body tissue vital at room resp body temperature. The invention can principally be applied in the fields of surgical transplantation, organ resp body tissue bank operation and research.

In clinical practice, it is known to "cold"-store free lobes of body tissue and isolated organs, which were extracted for transplantation into human beings, at 1° to 6° C. in cardioplegic solutions in order to reduce oxygen consumption and, thus, metabolism to a minimum. When doing so, free lobes of muscles, skin and/or bones shall be stored for a period not exceeding 24 hours before they are joined to a blood circulation again. In conjunction with animal experiments, maximum conservation periods of 45 hours have hitherto been attained.

These known solutions have the drawback of requisite cooling being laborious as well as the maximum conservation period being relatively short.

With organ conservation by means of hypothermal perfusion, it, furthermore, is known to make use of specific conservation solutions, such as are described in W. Konertz, Konservierung des Herzens zu Transplantationszwecken mit Euro-Collins-Lösungen, Habilitation Thesis, Kiel, 1987. Dialysis procedures, such as have become known in connection with application of the man-made kidney, are likewise notorious.

With the known solutions, long-term conservation of organs, body extremities resp lobes of body tissue is not possible at room temperature.

It, therefore, is the object of the invention to provide a method and a device which enable effective and economic long-term conservation of organs, body extremities and lobes of body tissue at room temperature resp body temperature.

It, furthermore, is the object of the invention to improve the preconditions of efficient research and to minimise the number of requisite animal experiments.

In accordance with the invention, this object is solved by the features in the characterising part of claims 1 and 7 in conjunction with the features of the respective preambles. Practical developments of the invention can be found in the subclaims.

The special advantage of the invention resides in that long-term conservation of organs, body extremities or lobes of body tissue in the order of 8 days and more is made possible at room resp body temperature. At these temperatures, metabolism continues and preserves activity of the fibroplastics for wound healing and accretion. For instance, free lobes of body tissue can be caused to accrete through an extracorporal circulation system, and that without any microsurgical joining of vessels.

Oxygen supply and detoxication, therewith, are brought about through three discrete circulation systems, the first circulation system supplying the organs, body extremities resp lobes of body tissue with an oxygen-rich arterial perfusate and oxygenising as well as detoxicating the venous perfusate and exchanging metabolites; the physiological aqueous solution of the second circulation system being oxygenised in a dilution pot and delivering the oxygen on the dialysis membrane or before the latter to the first circulation system in the liquid phase and the third circulation system realising discontinuous cleaning-by-flushing of the organs resp lobes of body tissue with a physiological aqueous solution and the three circulation systems being controlled such that either only circulation systems 1 and 2 will jointly be in operation or circulation system 3 will be in operation.

As perfusate, aqueous nutritive solutions or blood or blood products may be used.

Another advantage of the invention resides in that animal experiments can be reduced because examinations can be carried out on isolated organs and blocks of body tissue, which, otherwise, would result in an animal experiment. It is also possible that several teams work with the same organs of an animal.

A standardised model for examinations on isolated organs and free lobes is available for research. Banks for isolated organs and free blocks of body tissue may be installed. Organs and lobes of body tissue may be stored without a substantial phase of hypoxia and conditioned prior to transplantation.

Effective and economic performance of the method is achieved by a device with which an organ chamber has at least one arterial inlet, which is connected with the delivery section of a first pump, and at least one venous outlet, which is connected with the intake section of a second pump, as well as at least one entrance for the flushing agent and at least one exit for the flushing agent as well as at least one control entrance. The delivery section of the second pump is connected with the intake section of the first pump through a haemofilter.

In order to effectively guard the body tissue from microbial contamination, the organ chamber is manufactured so as to be air-tight and all hoses are made either of expendable material or consist of sterilisable material. In addition to all that, the organ chamber is made of at least partially transparent material. The third circulation system, controlled by a timer, is automatically switched on for cleaning the body tissue by flushing. During flushing, the first and second circulation systems are switched off in order to not adulterate the liquid.

In the following, the invention shall be explained in more detailed a manner on the basis of embodiments represented in the Figures.

Figure 2:
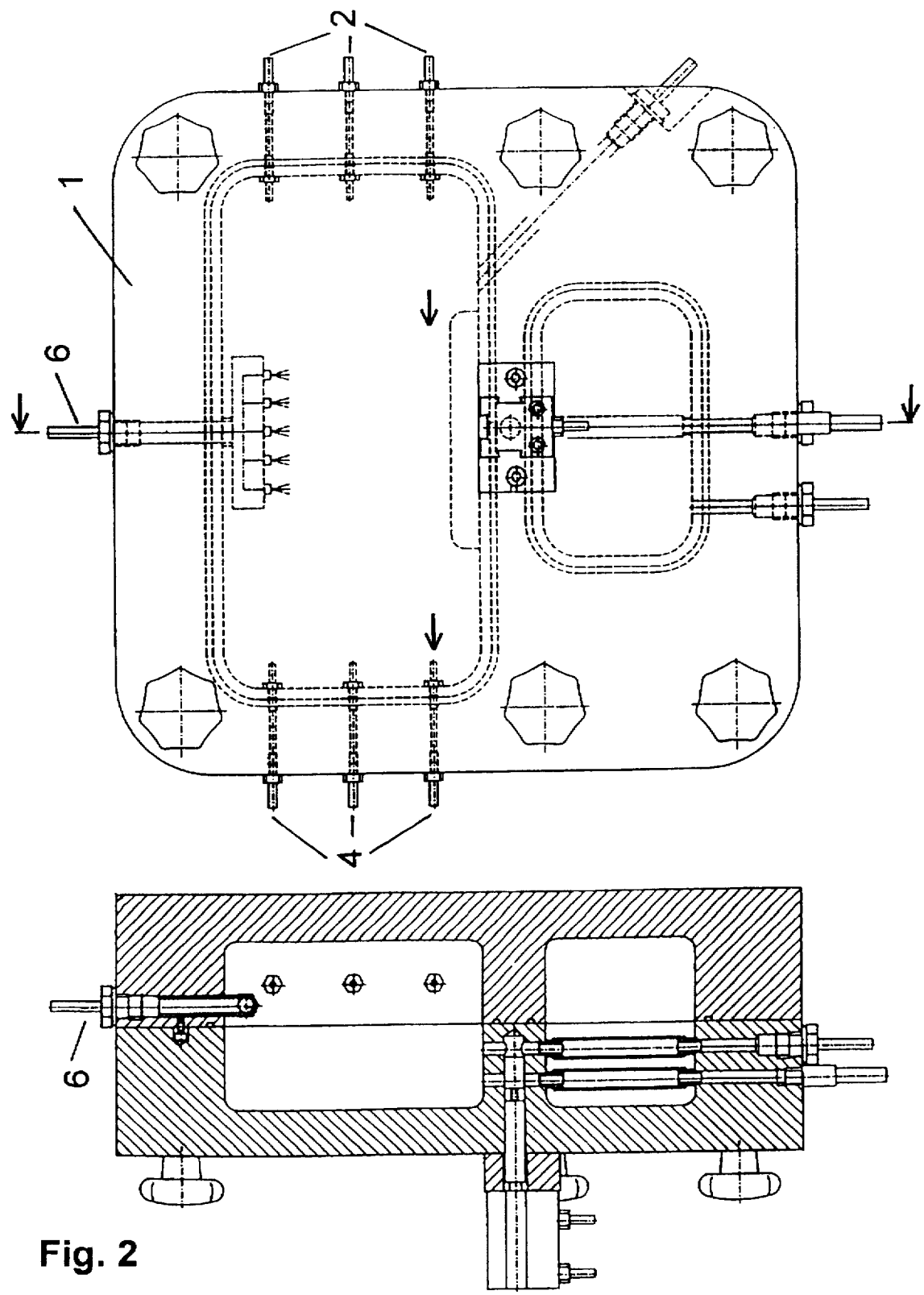
Figure 3:
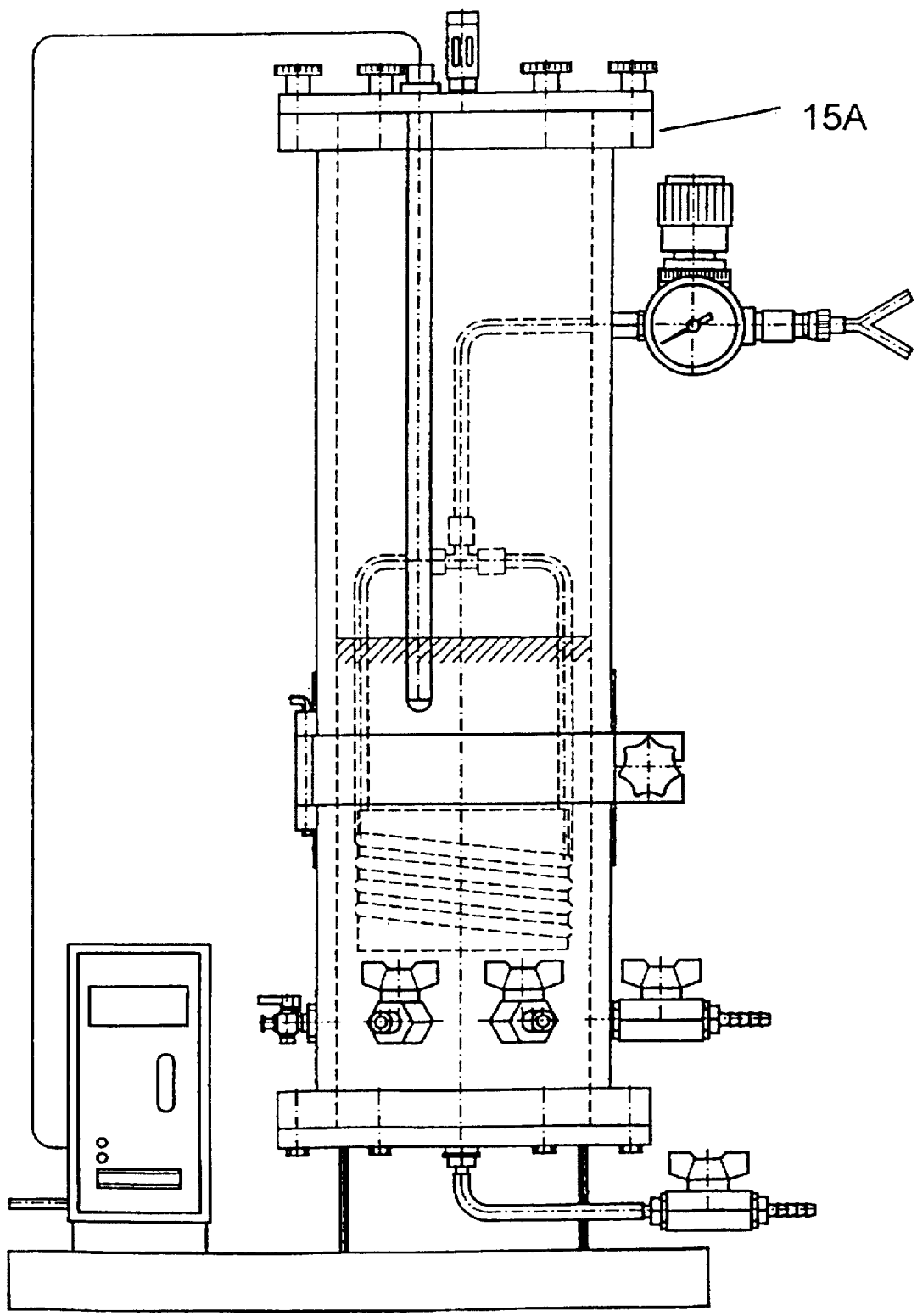

There show:

FIG. 1 a flow diagram of a conservation device with organ chamber and circulation systems;

FIG. 2 two different views of the organ chamber;

FIG. 3 the dilution pot from the dilution circulation system.

In accordance with FIG. 1, three discrete circulation systems are realised for conserving the organs, body extremities or lobes of body tissue which are situated in the organ chamber (1), the movement of the liquids being brought about by pumps, preferably by peristaltic pumps.

For this purpose, the venous outlets (4) of the organ chamber (1) are, through hoses, connected with a reservoir (12) for nutrient solution. The reservoir (12) is coupled with a pair of scales (13). From the pair of scales (13), a hose extends to the intake section (5a) of the pump (5), the delivery section (5b) of which is connected with the haemofilter (9) through a pressure meter (14). The haemofilter (9) is, furthermore, connected with the intake section (3a) of a pump (3), the delivery section (3b) of which being connected with the arterial inlet (2) of the organ chamber (1) through an air trap (10) with a vent (10a) and through a further pressure meter (11).

Connected to the haemofilter (9) is a dilution circulation system (15) with a dilution pot (15a). For realising the third circulation system, the organ chamber (1), furthermore, shows an entrance (6) for the flushing agent and an exit (7) for the flushing agent, said entrance (6) being connected with an antibiotic flushing reservoir (16) and said exit (7) being connected with a vessel (17) for rejected flushing liquid. Control of the circulation systems is effected through an electric control circuit (18) connected to the control entrance (8).

The way of functioning of the extracorporal circulation system shall hereinafter be explained in more detail.

Through the pump (3), the first circulation system supplies the organ, the body extremity or the lobe of body tissue with oxygen-rich perfusate. The second circulation system moves the liquid designated as dialysate in physiological concentration which, in a dilution reservoir, is oxygenised in hyperbaric or normobaric a manner and, then, oxygenises the organ perfusion liquid on a dialysis membrane as well as exchanges and detoxicates metabolites.

The method can be performed according to the dialysis or haemofiltration principle. Due to concentration polarisation of the proteins, the flows that can be achieved with the haemofiltration method are not so high as in case of the dialysis method.

As perfusate, blood, blood products or aqueous nutritive solutions come into question. In case of lobes of skin, muscles and/or bones, supply of oxygen in aqueous form is possible, provided that the rate of flow is correspondingly high.

The third circulation system provides for regular cleaning of the body tissue by flushing. It is switched through a time switch not illustrated in the Figures at intervals so that the liquids cannot be adulterated. As long as the flushing process is running, the circulation systems 1 and 2 are stopped.

Such cleaning-by-flushing and preservation of the body tissue in an organ chamber (1) which is manufactured so as to be a sterilisable and air-tight transparent vessel are necessary in order to avoid microbial contamination of the body tissue. For this reason, all liquid-carrying hoses are made of expendable products and the liquids of circulation systems 1 and 2 must, for hygienic reasons and for substrate renewal, be exchanged daily.

The successful function of the invention has, up to now, been made evident on the basis of animal experiments. A musculocutaneous trapezius lobe of a pig, therewith, served as model of a lobe of body tissue.

The invention is not limited to the embodiments as described in the aforegoing. Rather it is possible to realise other forms of construction without leaving the scope of the invention.

I claim:

1. Method of conserving a body part, such as organs, body extremities and lobes of body tissue, at a temperature inclusively between room temperature and body temperature, by utilizing an extracorporal circulation system having several circuits and without employing natural organs as a component part of the extracorporal circulation system, comprising the following steps:
   (1) in a first circuit supplying the body part with an oxygen-rich arterial perfusate, oxygenizing and detoxicating a venous perfusate and bringing about metabolite exchange,
   (2) in a second circuit, oxygenizing a first physiological aqueous solution in a dilution reservoir and effecting an oxygen transfer from said first, oxygenized solution of the second circuit to the first circuit and
   (3) in a third circuit, effecting a cleaning-by-flushing of the body part with a second physiological aqueous flushing solution wherein the circuits are controlled such that either only the first circuit and the second circuit together, or the third path alone, will be in operation at any one time.

2. Method as set forth in claim 1, wherein the oxygen contained in the arterial perfusate of the first circuit is furnished from the second circuit through a dialysis membrane.

3. Method as set forth in claim 1, wherein the perfusate of the first circuit consists of one or more of an aqueous nutritive solutions, blood, and blood products.

4. Method as set forth in claim 2, wherein detoxication and metabolite exchange are effected on the dialysis membrane.

5. Method as set forth in claim 2, wherein oxygenizing is effected in either a normobaric or hyperbaric manner.

6. Method as set forth in claim 1, wherein movement of the fluid through the circuits is brought about by pumps.

7. Device for conserving body parts, such as organs, body extremities and lobes of body tissue, said device comprising three circuits and not using natural organs as a component part of the device, the device comprising an organ chamber for holding the body part to be conserved, the organ chamber comprising a first circuit comprising at least one arterial inlet connected to a delivery section of a first pump, a second circuit comprising at least one venous outlet connected to an intake section of a second pump, a third circuit comprising at least one entrance for a flushing agent and at least one exit for the flushing agent, and at least one control entrance, wherein a delivery section of the second pump is connected to the intake section of the first pump through an oxygen transfer means.

8. Device as defined in claim 7, wherein the circuits are interconnected by hoses consisting of either expendable material or sterilizable material.

9. Device as defined in claim 7, wherein between the arterial inlet of the organ chamber and the delivery section of the first pump, there is disposed an air trap with a vent as well as a pressure meter for measuring organ pressure.

10. Device as defined in claim 7, wherein between the venous outlet, the organ chamber and the intake section of the second pump, there is disposed a reservoir for nutrient solution and at least one scale.

11. Device as defined in claim 7, wherein between the delivery section of the second pump and an entrance of the oxygen transfer means, there is disposed a pressure meter.

12. Device as defined in claim 7, wherein a dilution circuit is joined to the oxygen transfer means.

13. Device as defined in claim 7, wherein the entrance for the flushing agent is connected to a flushing agent reservoir.

14. Device as defined in claim 7, wherein the exit for the flushing agent is connected to a vessel for receiving rejected flushing liquid.

15. Device as defined in claim 7, wherein the control entrance is connected to an electric control circuit through a pressure line.

16. Device as defined in claim 7, wherein the organ chamber is a transparent, air-tight vessel.

17. Device as defined in claim 7, wherein the first and second pumps are one or more of a peristaltic, a roller pump, and a small pump, of the type employed with a man-made heart.

18. Method as set forth in claim 2, wherein the perfusate of the first circuit consists of at least one of the aqueous nutritive solution, blood, and blood products.

19. Method as set forth in claim 2, wherein detoxication and metabolite exchange are effected on the dialysis membrane.

20. Method as set forth in claim 4, wherein oxygenizing is effected in a normobaric or hyperbaric manner.

* * * * *